US007538166B2

(12) United States Patent
Tanaka et al.

(10) Patent No.: US 7,538,166 B2
(45) Date of Patent: May 26, 2009

(54) EPOXY COMPOUNDS AND CURED EPOXY RESINS OBTAINED BY CURING THE COMPOUNDS

(75) Inventors: Shinya Tanaka, Toyono-gun (JP); Yoshitaka Takezawa, Hitachi (JP); Hiroyuki Takahashi, Hitachi (JP)

(73) Assignees: Sumitomo Chemical Company, Limited, Tokyo (JP); Hitachi, Ltd., Tokyo (JP)

( * ) Notice: Subject to any disclaimer, the term of this patent is extended or adjusted under 35 U.S.C. 154(b) by 29 days.

(21) Appl. No.: 10/584,307

(22) PCT Filed: Dec. 22, 2004

(86) PCT No.: PCT/JP2004/019186

§ 371 (c)(1),
(2), (4) Date: Jun. 23, 2006

(87) PCT Pub. No.: WO2005/061473

PCT Pub. Date: Jul. 7, 2005

(65) Prior Publication Data

US 2007/0184280 A1      Aug. 9, 2007

(30) Foreign Application Priority Data

Dec. 24, 2003    (JP) ............................. 2003-426610

(51) Int. Cl.
*C08G 59/04* (2006.01)
*B32B 27/04* (2006.01)
(52) U.S. Cl. ...................... 525/523; 428/413; 428/297.4
(58) Field of Classification Search .................. 428/413, 428/297.4; 525/523
See application file for complete search history.

(56) References Cited

U.S. PATENT DOCUMENTS

| 3,461,098 | A |   | 8/1969 | Cotter et al. |
|---|---|---|---|---|
| 5,189,117 | A |   | 2/1993 | Hefner, Jr. |
| 5,525,433 | A |   | 6/1996 | Poutasse et al. |
| 5,560,864 | A |   | 10/1996 | Goulding |
| 5,569,727 | A |   | 10/1996 | Mormann et al. |
| 5,629,098 | A |   | 5/1997 | Poutasse et al. |
| 5,750,051 | A |   | 5/1998 | Goulding et al. |
| 5,773,178 | A | * | 6/1998 | Shiota et al. ............... 430/20 |
| 5,811,504 | A |   | 9/1998 | Shiota et al. |
| 5,851,427 | A |   | 12/1998 | Kelly |
| 5,904,984 | A |   | 5/1999 | Smith et al. |
| 6,143,379 | A | * | 11/2000 | Schoenfeld et al. .......... 428/1.1 |
| 6,229,675 | B1 | * | 5/2001 | Tanaka et al. ............... 360/265 |
| 6,312,769 | B1 | * | 11/2001 | Hiraoka et al. .............. 428/1.1 |
| 6,326,555 | B1 | * | 12/2001 | McCormack et al. ....... 174/255 |
| 6,539,171 | B2 | * | 3/2003 | VonArx et al. .............. 392/451 |
| 6,748,646 | B2 | * | 6/2004 | Von Arx et al. ............. 29/613 |
| 6,780,493 | B2 | * | 8/2004 | Noda et al. .................. 428/209 |
| 6,872,858 | B2 |   | 3/2005 | Muragaki et al. |

| 2002/0077046 | A1 | * | 6/2002 | Nanjo et al. ................. 451/291 |
|---|---|---|---|---|
| 2002/0127006 | A1 | * | 9/2002 | Tweedy et al. .............. 392/451 |

FOREIGN PATENT DOCUMENTS

| EP | 503856 A1 | * | 9/1992 |
|---|---|---|---|
| GB | 2 315 760 |   | 2/1998 |
| GB | 2 329 899 |   | 4/1999 |
| GB | 2 329 900 |   | 4/1999 |
| GB | 2 330 360 |   | 4/1999 |
| GB | 2 338 240 |   | 12/1999 |
| JP | 63-69255 |   | 3/1988 |
| JP | 1-168632 |   | 7/1989 |
| JP | 1-168634 |   | 7/1989 |
| JP | 2-212449 |   | 8/1990 |
| JP | 7-15620 |   | 1/1995 |
| JP | 7-156020 |   | 6/1995 |
| JP | 7-508797 |   | 9/1995 |
| JP | 7-258638 |   | 10/1995 |
| JP | 7-316526 |   | 12/1995 |
| JP | 8-277247 |   | 10/1996 |
| JP | 9-118673 |   | 5/1997 |
| JP | 2002-212265 |   | 7/2002 |
| JP | 2002-363117 |   | 12/2002 |
| JP | 2003-82061 |   | 3/2003 |
| JP | 2005-29788 |   | 2/2005 |
| WO | 2004/113327 |   | 12/2004 |

OTHER PUBLICATIONS

Bezborodov and Petrov. Liquid crystalline 1,4-disubstituted cyclohexenylene derivatives. Liquid Crystals. vol. 26, Issue 2, pp. 271-280. Sep. 1999.*

(Continued)

*Primary Examiner*—Mark Eashoo
*Assistant Examiner*—Megan McCulley
(74) *Attorney, Agent, or Firm*—Wenderoth, Lind & Ponack, L.L.P.

(57) ABSTRACT

Novel epoxy compounds represented by the general formula (1)

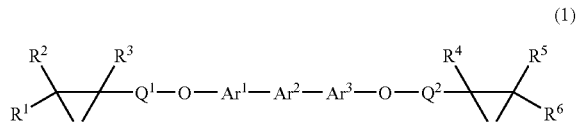

(1)

wherein $Ar^1$, $Ar^2$ and $Ar^3$ are each optionally substituted phenylene, cyclohexanyl or the like, $R^1$, $R^2$, $R^3$, $R^4$, $R^5$ and $R^6$ are each hydrogen or alkyl of 1 to 18 carbon atoms, and $Q^1$ and $Q^2$ are each alkylene of 1 to 9 carbon atoms or the like, which are useful as the raw material of cured epoxy resins exhibiting liquid crystallinity; a process for the production thereof; and compositions containing the compounds.

10 Claims, No Drawings

OTHER PUBLICATIONS

Marcus J. Watson et al., "A phenomenological approach to the inversion of the helical twist sense in the chiral nematic phase", J. Matter Chem, 8(9), pp. 1963-1969, 1998.

N. Barashkov et al., "Design of New Polymers to Improve Radiation Stability of Plastic Scintillators", Proceedings of the Fourth International Conference on Calorimetry in High Energy Physics, XP009037802, pp. 542-551, 1993.

English Translation of First Office Action issued Jul. 4, 2008 in Chinese Patent Application No. 200480038664.1 corresponding to the present U.S. application.

* cited by examiner

EPOXY COMPOUNDS AND CURED EPOXY RESINS OBTAINED BY CURING THE COMPOUNDS

TECHNICAL FIELD

The present invention relates to epoxy compounds and cured epoxy resins obtained by curing the compounds.

BACKGROUND ART

It is known that a cured epoxy resin obtained by curing an epoxy compound having mesogenic groups with the use of a curing agent such as a diamine compound exhibits liquid crystallinity (for example, see JP-A 9-118673). However, it is difficult to cure such an epoxy resin by melt blending at the curing temperature or below with the use of a curing agent such as diaminodiphenylmethane because of its high melting temperature.

DISCLOSURE OF INVENTION

Problem to be Solved by the Invention

Under the circumstances, the present inventors intensively studied in order to develop novel epoxy compounds which are useful as the raw material of cured epoxy resins exhibiting liquid crystallinity and have lower melting temperatures. As a result, they found that an epoxy compound represented by the formula (1):

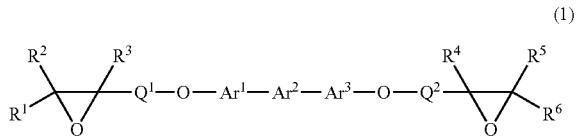

wherein
$Ar^1$, $Ar^2$ and $Ar^3$ are the same or different and each denotes any one of divalent groups represented by the following formulas:

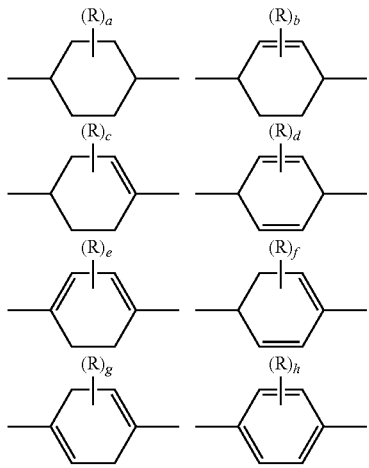

in which m denotes an integer of 1 to 9, R denotes a hydrogen atom or an alkyl group of 1 to 18 carbon atoms, a denotes an integer of 1 to 8, b, e and g denote an integer of 1 to 6, c denotes an integer of 1 to 7, d and h denote an integer of 1 to 4, and f denotes an integer of 1 to 5, and when more than one R exists in said divalent group, all of R may be the same group or different groups;

$R^1$, $R^2$, $R^3$, $R^4$, $R^5$ and R6 are the same or different and each denotes a hydrogen atom or an alkyl group of 1 to 18 carbon atoms;

$Q^1$ and $Q^2$ are the same or different and each denotes a straight-chain alkylene group of 1 to 9 carbon atoms, in which methylene groups composing the straight-chain alkylene group are optionally substituted with an alkyl group of 1 to 18 carbon atoms and —O— or —N(R$_7$)— is optionally inserted between the methylene groups, in which $R^7$ denotes a hydrogen atom or an alkyl group of 1 to 18 carbon atoms; had a lower melt temperature and a cured epoxy resin obtained by curing the compound exhibited liquid crystallinity, and then they completed the present invention.

Means for Solving the Problem

That is to say, the present invention provides an epoxy compound represented by the following formula (1):

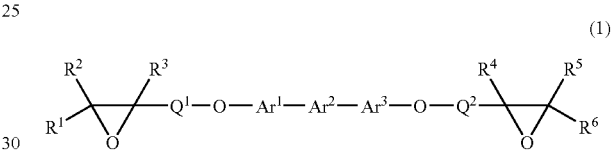

wherein
$Ar^1$, $Ar^2$ and $Ar^3$ are the same or different and each denotes any one of divalent groups represented by the following formulas:

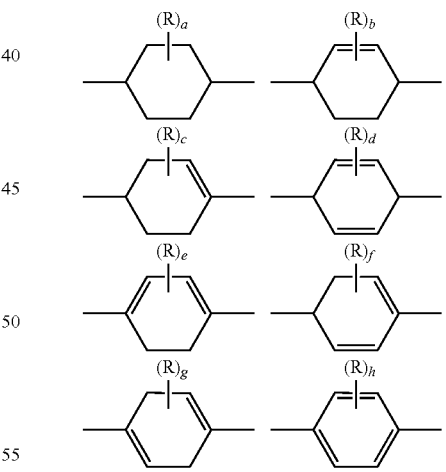

in which m denotes an integer of 1 to 9, R denotes a hydrogen atom or an alkyl group of 1 to 18 carbon atoms, a denotes an integer of 1 to 8, b, e and g denote an integer of 1 to 6, c denotes an integer of 1 to 7, d and h denote an integer of 1 to 4, and f denotes an integer of 1 to 5, and when more than one R exists in said divalent group, all of R may be the same group or different groups;

$R^1$, $R^2$, $R^3$, $R^4$, $R^5$ and R6 are the same or different and each denotes a hydrogen atom or an alkyl group of 1 to 18 carbon atoms;

$Q^1$ and $Q^2$ are the same or different and each denotes a straight-chain alkylene group of 1 to 9 carbon atoms, in which methylene groups composing the straight-chain alkylene group are optionally substituted with an alkyl group of 1 to 18 carbon atoms and —O— or —N($R^7$)— is optionally inserted between the methylene groups, in which $R^7$ denotes a hydrogen atom or an alkyl group of 1 to 18 carbon atoms; and a cured epoxy resin obtained by curing the compound with the use of a curing agent.

Effect of the Invention

The epoxy compound of the present invention has a lower melting temperature and can be melt-blended with a curing agent at the curing temperature or below. A cured epoxy resin obtained by curing the epoxy compound of the present invention with the use of a curing agent not only exhibits liquid crystallinity, but also has a high thermal conductivity, so that it is useful as an insulating material which requires a high heat dissipation capacity, such as a printed wiring board.

Best Mode for Carrying Out the Invention

In the epoxy compound of the present invention represented by the following formula (1) (hereinafter abbreviated as the epoxy compound (1)):

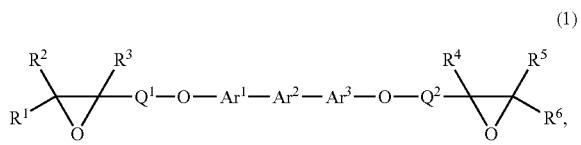

(1)

$Ar^1$, $Ar^2$ and $Ar^3$ are the same or different and each denotes any one of divalent groups represented by the following formulas:

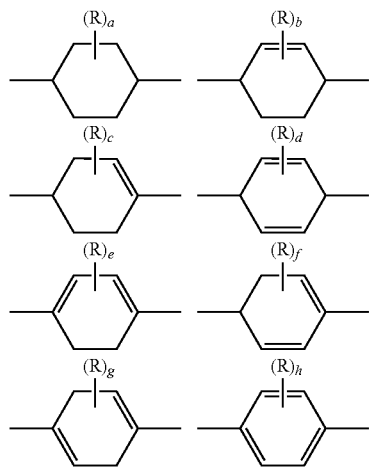

in which R denotes a hydrogen atom or an alkyl group of 1 to 18 carbon atoms, a denotes an integer of 1 to 8, b, e and g denote an integer of 1 to 6, c denotes an integer of 1 to 7, d and h denote an integer of 1 to 4, and f denotes an integer of 1 to 5, and when more than one R exists in said divalent group, all of R may be the same group or different groups;

$R^1$, $R^2$, $R^3$, $R^4$, $R^5$ and $R^6$ are the same or different and each denotes a hydrogen atom or an alkyl group of 1 to 18 carbon atoms;

$Q^1$ and $Q^2$ are the same or different and each denotes a straight-chain alkylene group of 1 to 9 carbon atoms, in which methylene groups composing the straight-chain alkylene group are optionally substituted with an alkyl group of 1 to 18 carbon atoms and —O— or —N($R^7$)— is optionally inserted between the methylene groups, in which $R^7$ denotes a hydrogen atom or an alkyl group of 1 to 18 carbon atoms.

Examples of the alkyl group of 1 to 18 carbon atoms include straight-chain or branched-chain alkyl groups of 1 to 18 carbon atoms such as methyl, ethyl, n-propyl, isopropyl, n-butyl, isobutyl, sec-butyl, tert-butyl, n-pentyl, n-hexyl, n-octyl, isooctyl, n-decyl, n-dodecyl, n-pentadecyl, n-octadecyl group and the like.

Examples of the above-mentioned divalent groups include cyclohexane-1,4-diyl, 2-cyclohexene-1,4-diyl, 1-cyclohexene-1,4-diyl, 1,4-cyclohexadiene-3,6-diyl, 1,3-cyclohexadiene-1,4-diyl, 1,3-cyclohexadiene-2,5-diyl, 1,4-cyclohexadiene-1,4-diyl, 1,4-phenylene, 2-methylcyclohexane-1,4-diyl, 3-methyl-1,4-phenylene group and the like.

Examples of the straight-chain alkylene group of 1 to 9 carbon atoms include groups formed by bonding 1 to 9 methylene groups linearly, such as methylene, ethylene, trimethylene, tetramethylene, hexamethylene, nonamethylene group and the like. The methylene groups composing such a straight-chain alkylene group of 1 to 9 carbon atoms are optionally substituted with an alkyl group of 1 to 18 carbon atoms, and —O— or —N($R^7$)— is optionally inserted between the methylene groups. Examples of such an alkylene group in which the methylene groups are substituted with an alkyl group of 1 to 18 carbon atoms or in which —O— or —N($R^7$)— is inserted between the methylene groups include 2-methyltrimethylene, 1,2-dimethylethylene, 3-oxatetramethylene, 3-oxapentamethylene group and the like.

Among the epoxy compounds (1), preferred is an epoxy compound represented by the formula (2):

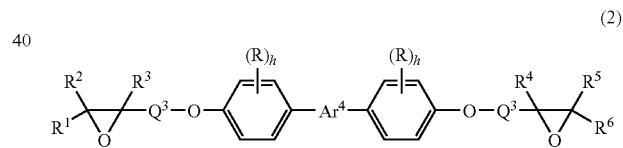

(2)

wherein $Ar^4$ denotes any one of divalent groups represented by the following formulas:

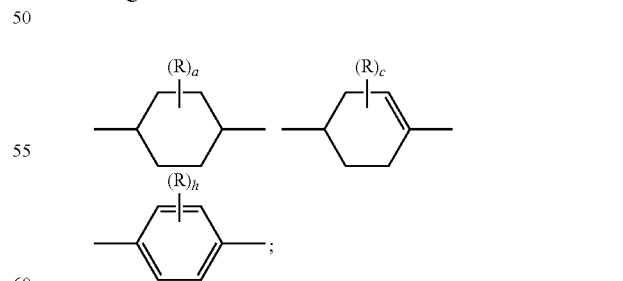

R, $R^1$, $R^2$, $R^3$, $R^4$, $R^5$, $R^6$, a, c and h are as defined above; and $Q^3$ denotes any one of groups represented by the following formulas:

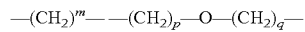

in which m denotes an integer of 1 to 9, p and q denote an integer of 1 to 8, and the sum of p and q is 9 or less, and methylene groups composing the group represented by $Q^3$ are optionally substituted with an alkyl group of 1 to 18 carbon atoms. Among them, an epoxy compound in which $R^1$, $R^2$, $R^3$, $R^4$, $R^5$ and $R^6$ are hydrogen atoms is particularly preferred.

Examples of the epoxy compound (1) include 1,4-bis{4-(oxiranylmethoxy)phenyl}-1-cyclohexene, 1-{3-methyl-4-(oxiranylmethoxy)phenyl}-4-{4-(oxiranylmethoxy)phenyl}-1-cyclohexene, 1-{2-methyl-4-(oxiranylmethoxy)phenyl}-4-{4-(oxiranylmethoxy)phenyl}-1-cyclohexene, 1-{3-ethyl-4-(oxiranylmethoxy)phenyl}-4-{4-(oxiranylmethoxy)phenyl}-1-cyclohexene, 1-{2-ethyl-4-(oxiranylmethoxy)phenyl}-4-{4-(oxiranylmethoxy)phenyl}-1-cyclohexene, 1-{3-n-propyl-4-(oxiranylmethoxy)phenyl}-4-{4-(oxiranylmethoxy)phenyl}-1-cyclohexene, 1-{3-isopropyl-4-(oxiranylmethoxy)phenyl}-4-{4-(oxiranylmethoxy)phenyl}-1-cyclohexene, 1,4-bis{4-(oxiranylmethoxy)phenyl}-2-cyclohexene, 1-{3-methyl-4-(oxiranylmethoxy)phenyl}-4-{4-(oxiranylmethoxy)phenyl}-2-cyclohexene, 1,4-bis{4-(oxiranylmethoxy)phenyl}-2,5-cyclohexadiene, 1-{3-methyl-4-(oxiranylmethoxy)phenyl}-4-{4-(oxiranylmethoxy)phenyl}-2,5-cyclohexadiene, 1,4-bis{4-(oxiranylmethoxy)phenyl}-1,5-cyclohexadiene, 1-{3-methyl-4-(oxiranylmethoxy)phenyl}-4-{4-(oxiranylmethoxy)phenyl}-1,5-cyclohexadiene, 1,4-bis{4-(oxiranylmethoxy)phenyl}-1,4-cyclohexadiene, 1-{3-methyl-4-(oxiranylmethoxy)phenyl}-4-{4-(oxiranylmethoxy)phenyl}-1,4-cyclohexadiene, 1,4-bis{4-(oxiranylmethoxy)phenyl}-1,3-cyclohexadiene, 1-{3-methyl-4-(oxiranylmethoxy)phenyl}-4-{4-(oxiranylmethoxy)phenyl}-1,3-cyclohexadiene, 1,4-bis{4-(oxiranylmethoxy)phenyl}benzene, 1-{3-methyl-4-(oxiranylmethoxy)phenyl}-4-{4-(oxiranylmethoxy)phenyl}benzene, 1,4-bis{4-(oxiranylmethoxy)phenyl}cyclohexane, 1-{3-methyl-4-(oxiranylmethoxy)phenyl}-4-{4-(oxiranylmethoxy)phenyl}cyclohexane, 1,4-bis{4-(3-oxa-5,6-epoxyhexyloxy)phenyl}-1-cyclohexene, 1-{4-(3-oxa-5,6-epoxyhexyloxy)-3-methylphenyl}-4-{4-(3-oxa-5,6-epoxyhexyloxy)phenyl}-1-cyclohexene, 1,4-bis{4-(5-methyl-3-oxa-5,6-epoxyhexyloxy)phenyl}-1-cyclohexene, 1-{4-(5-methyl-3-oxa-5,6-epoxyhexyloxy)-3-methylphenyl}-4-{4-(5-methyl-3-oxa-5,6-epoxyhexyloxy)phenyl}-1-cyclohexene, 1,4-bis{4-(4-methyl-4,5-epoxypentyloxy)phenyl}-1-cyclohexene, 1,4-bis{4-(3-oxa-5,6-epoxyhexyloxy)phenyl}benzene, 1-{4-(3-oxa-5,6-epoxyhexyloxy)-3-methylphenyl}-4-{4-(3-oxa-5,6-epoxyhexyloxy)phenyl}benzene, 1,4-bis{4-(5-methyl-3-oxa-5,6-epoxyhexyloxy)phenyl}benzene, 1-{4-(5-methyl-3-oxa-5,6-epoxyhexyloxy)-3-methylphenyl}-4-{4-(5-methyl-3-oxa-5,6-epoxyhexyloxy)phenyl}benzene, 1,4-bis{4-(4-methyl-4,5-epoxypentyloxy)phenyl}benzene, 1,4-bis{4-(3-oxa-5,6-epoxyhexyloxy)phenyl}cyclohexane, 1-{4-(3-oxa-5,6-epoxyhexyloxy)-3-methylphenyl}-4-{4-(3-oxa-5,6-epoxyhexyloxy)phenyl}cyclohexane, 1,4-bis{4-(5-methyl-3-oxa-5,6-epoxyhexyloxy)phenyl}cyclohexane, 1-{4-(5-methyl-3-oxa-5,6-epoxyhexyloxy)-3-methylphenyl}-4-{4-(5-methyl-3-oxa-5,6-epoxyhexyloxy)phenyl}cyclohexane, 1,4-bis{4-(4-methyl-4,5-epoxypentyloxy)phenyl}cyclohexane, and the like.

Among them, preferred are 1,4-bis{4-(oxiranylmethoxy)phenyl}-1-cyclohexene, 1-{3-methyl-4-(oxiranylmethoxy)phenyl}-4-{4-(oxiranylmethoxy)phenyl}-1-cyclohexene, 1-{2-methyl-4-(oxiranylmethoxy)phenyl}-4-{4-(oxiranylmethoxy)phenyl}-1-cyclohexene, 1-{3-ethyl-4-(oxiranylmethoxy)phenyl}-4-{4-(oxiranylmethoxy)phenyl}-1-cyclohexene, 1-{2-ethyl-4-(oxiranylmethoxy)phenyl}-4-{4-(oxiranylmethoxy)phenyl}-1-cyclohexene, 1-{3-n-propyl-4-(oxiranylmethoxy)phenyl}-4-{4-(oxiranylmethoxy)phenyl}-1-cyclohexene, 1-{3-isopropyl-4-(oxiranylmethoxy)phenyl}-4-{4-(oxiranylmethoxy)phenyl}-1-cyclohexene, 1,4-bis{4-(oxiranylmethoxy)phenyl}benzene, 1-{3-methyl-4-(oxiranylmethoxy)phenyl}-4-{4-(oxiranylmethoxy)phenyl}benzene, 1,4-bis{4-(oxiranylmethoxy)phenyl}cyclohexane, 1-{3-methyl-4-(oxiranylmethoxy)phenyl}-4-{4-(oxiranylmethoxy)phenyl}cyclohexane, 1,4-bis{4-(3-oxa-5,6-epoxyhexyloxy)phenyl}-1-cyclohexene, 1-{4-(3-oxa-5,6-epoxyhexyloxy)-3-methylphenyl}-4-{4-(3-oxa-5,6-epoxyhexyloxy)phenyl}-1-cyclohexene, 1,4-bis{4-(3-oxa-5,6-epoxyhexyloxy)phenyl}benzene, 1-{4-(3-oxa-5,6-epoxyhexyloxy)-3-methylphenyl}-4-{4-(3-oxa-5,6-epoxyhexyloxy)phenyl}benzene, 1,4-bis{4-(3-oxa-5,6-epoxyhexyloxy)phenyl}cyclohexane and 1-{4-(3-oxa-5,6-epoxyhexyloxy)-3-methylphenyl}-4-{4-(3-oxa-5,6-epoxyhexyloxy)phenyl}cyclohexane.

Next, a method for producing the epoxy compound (1) is described. The epoxy compound (1) is produced, for example, by reacting a compound represented by the formula (3):

$$HO-Ar^1-Ar^2-Ar^3-OH \qquad (3)$$

wherein $Ar^1$, $Ar^2$ and $Ar^3$ are as defined above (hereinafter abbreviated as the compound (3)), a compound represented by the formula (4):

(4)

wherein $R^1$, $R^2$ and $R^3$ are the same or different and each denotes a hydrogen atom or an alkyl group of 1 to 18 carbon atoms, $Q^1$ denotes a straight-chain alkylene group of 1 to 9 carbon atoms, in which methylene groups composing the straight-chain alkylene group are optionally substituted with an alkyl group of 1 to 18 carbon atoms and —O— or —N($R^7$)— is optionally inserted between the methylene groups, in which $R^7$ denotes a hydrogen atom or an alkyl group of 1 to 18 carbon atoms, and $X^1$ denotes a halogen atom (hereinafter abbreviated as the compound (4)), and a compound represented by the following formula (5):

(5)

wherein $R^4$, $R^5$ and $R^6$ are the same or different and each denotes a hydrogen atom or an alkyl group of 1 to 18 carbon atoms, $Q^2$ denotes a straight-chain alkylene group of 1 to 9 carbon atoms, in which methylene groups composing the straight-chain alkylene group are optionally substituted with an alkyl group of 1 to 18 carbon atoms and —O— or —N($R^7$)— is optionally inserted between the methylene groups, in which $R^7$ denotes a hydrogen atom or an alkyl group of 1 to 18 carbon atoms, and $X^2$ denotes a halogen atom (hereinafter abbreviated as the compound (5)), in the presence of a base; or by reacting the compound (3), a compound represented by the formula (6)

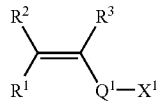
(6)

wherein $R^1$, $R^2$, $R^3$, $Q^1$ and $X^1$ are as defined above (hereinafter abbreviated as the compound (6)) and a compound represented by the formula (7)

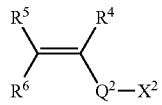
(7)

wherein $R^4$, $R^5$, $R^6$, $Q^2$ and $X^2$ are as defined above (hereinafter abbreviated as the compound (7)) in the presence of a base and then treating the reaction mixture with an oxidizing agent such as m-chloroperbenzoic acid. The former method comprising a reaction of the compound (3), the compound (4) and the compound (5) in the presence of a base is preferred.

First, a method for producing the compound (1) which comprises a reaction of the compound (3), the compound (4) and the compound (5) in the presence of a base is described. Examples of the compound (3) include 1,4-bis(4-hydroxyphenyl)-1-cyclohexene, 1-(3-methyl-4-hydroxyphenyl) -4-(4-hydroxyphenyl)-1-cyclohexene, 1,4-bis(4-hydroxyphenyl)-2-cyclohexene, 1-(3-methyl-4-hydroxyphenyl) -4-(4-hydroxyphenyl)-2-cyclohexene, 1,4-bis(4-hydroxyphenyl)-2,5-cyclohexadiene, 1-(3-methyl-4-hydroxyphenyl)-4-(4-hydroxyphenyl)-2,5-cyclohexadiene, 1,4-bis(4-hydroxyphenyl)-1,5-cyclohexadiene, 1-(3-methyl-4-hydroxyphenyl)-4-(4-hydroxyphenyl)-1,5-cyclohexadiene, 1,4-bis(4-hydroxyphenyl)-1,4-cyclohexadiene, 1-(3-methyl-4-hydroxyphenyl)-4-(4-hydroxyphenyl)-1,4-cyclohexadiene, 1,4-bis(4-hydroxyphenyl)-1,3-cyclohexadiene, 1-(3-methyl-4-hydroxyphenyl)-4-(4-hydroxyphenyl)-1,3-cyclohexadiene, 1,4-bis(4-hydroxyphenyl)benzene, 1-(3-methyl-4-hydroxyphenyl) -4-(4-hydroxyphenyl)benzene, 1,4-bis(4-hydroxyphenyl)cyclohexan, 1-(3-methyl-4-hydroxyphenyl)-4-(4-hydroxyphenyl)cyclohexane and the like. The compound (3) can be produced according to a known method such as a method described in JP-A 1-168632, JP-A 1-168634, U.S. Pat. No. 3,461,098, JP-A 2-212449, JP-A 2002-234856, JP-A 2002-308809, JP-A 2002-363117 or JP-A 2003-12585.

Examples of the halogen atom include a chlorine atom, a bromine atom and the like. The compound (4) and the compound (5) may be the same or different. Examples of the compound (4) and the compound (5) include epichlorohydrin, epibromohydrin, 2-(chloroethyl)oxirane, 2-(bromoethyl)oxirane and the like.

In the case where the compound (4) and the compound (5) are the same, the amount used of the compound is usually 2 to 100 times, preferably 2 to 50 times the molar amount used of the compound (3). In the case where the compound (4) and the compound (5) are different, the amount used of the compound (4) is usually 1 to 50 times, preferably 1 to 25 times the molar amount used of the compound (3), and the amount used of the compound (5) is usually 1 to 50 times, preferably 1 to 25 times the molar amount used of the compound (3).

Examples of the base include inorganic bases such as sodium hydroxide and potassium hydroxide, and the amount used thereof is usually 2 to 5 times the molar amount used of the compound (3).

A reaction of the compound (3), the compound (4) and the compound (5) is usually performed by mixing the compound (3), the compound (4), the compound (5) and the base in a solvent. The order of mixing them is not particularly limited. In the case where the compound (4) and the compound (5) are different, it is preferable that the compound (3) and the compound (4) are reacted in the presence of the base and then reacted with the compound (5), or the compound (3) and the compound (5) are reacted in the presence of the base and then reacted with the compound (4).

The solvent is not particularly limited as long as it is inactive in the reaction, and however, a hydrophilic solvent is preferred on the ground of that production of by-products tends to be suppressed. Examples of the hydrophilic solvent include alcohol solvents such as methanol, ethanol, propanol, butanol, ethylene glycol and propylene glycol; ketone solvents such as methyl ethyl ketone and methyl isobutyl ketone; aprotic polar solvents such as N,N-dimethylformamide, dimethyl sulfoxide and N-methylpyrrolidone; ether solvents such as tetrahydrofuran, dioxane, methoxymethyl ether and diethoxyethane; and the like, and they may be used alone or in any combination. Among them, ether solvents, aprotic polar solvents and mixed solvents thereof are preferred, aprotic polar solvents are more preferred, and dimethyl sulfoxide is particularly preferred. The used amount of the solvent is usually 0.1 to 50 parts by weight, preferably 0.5 to 5 parts by weight per part by weight of the compound (3).

The reaction may be performed under normal pressure or reduced pressure. The reaction temperature is usually 10 to 150° C. In the reaction, by-product water is occasionally produced as the reaction progresses. In such case, the reaction is preferably performed while removing by-product water out of the reaction system, and the reaction temperature and reaction pressure are preferably the temperature and pressure at which by-product water is removed by azeotroping.

After completion of the reaction, the epoxy compound (1) can be isolated as a crystal, for example, by removing the remaining compound (4) and compound (5), adding a hydrophilic solvent if necessary, filtering off insolubles, and then cooling the filtrate. The isolated epoxy compound (1) may be further purified by a conventional purification means such as recrystallization.

Next, a method for producing the epoxy compound (1) which comprises reacting the compound (3), the compound (6) and the compound (7) in the presence of a base and then treating the reaction mixture with an oxidizing agent such as m-chloroperbenzoic acid is described.

The compound (6) and the compound (7) may be the same or different, and include allyl chloride, allyl bromide and the like.

In the case where the compound (6) and the compound (7) are the same, the amount used of the compound is usually 2 to 100 times, preferably 2 to 50 times the molar amount used of the compound (3). In the case where the compound (6) and the compound (7) are different, the amount used of the compound (6) is usually 1 to 50 times, preferably 1 to 25 times the molar amount used of the compound (3), and the amount used of the compound (7) is usually 1 to 50 times, preferably 1 to 25 times of the molar amount used of the compound (3).

Examples of the base include inorganic bases such as sodium hydroxide and potassium hydroxide, and organic bases such as pyridine, and the amount used thereof is usually 2 to 5 times the molar amount used of the compound (3). In the case of using the organic base in the liquid form under the reaction conditions, such an organic base may be also used as a reaction solvent in an excessive amount.

A reaction of the compound (3), the compound (6) and the compound (7) is usually performed by mixing the compound (3), the compound (6), the compound (7) and the base in a solvent. The order of mixing them is not particularly limited. In the case where the compound (6) and the compound (7) are different, it is preferable that the compound (3) and the compound (6) are reacted in the presence of the base and then reacted with the compound (7), or the compound (3) and the compound (7) are reacted in the presence of the base and then reacted with the compound (6).

Examples of the solvent are the same as mentioned above for the reaction of the compound (3) and the compound (4). As described above, in the case of using the organic base in the liquid form under the reaction conditions as the base, such an organic base may be also used as a reaction solvent.

After completion of the reaction, the reaction liquid may be directly treated with an oxidizing agent. Alternatively, the reaction liquid may be mixed with water and a reaction product of the compound (3), the compound (6) and the compound (7) may be then isolated, before the treatment with an oxidizing agent. The oxidizing agent is not particularly limited as long as it can oxidize a carbon-carbon double bond to an epoxy group, and includes m-chloroperbenzoic acid and the like. The used amount of the oxidizing agent is usually 2 to 10 times the molar amount of a reaction product of the compound (3), the compound (6) and the compound (7).

After the treatment with an oxidizing agent, the epoxy compound (1) can be isolated, for example, by decomposing the remaining oxidizing agent in the reaction liquid if necessary and then concentrating the reaction liquid.

Among the epoxy compounds (1), an epoxy compound wherein $Q^1$ and $Q^2$ are the same or different and each is a straight-chain alkylene group of 1 to 9 carbon atoms, and —O— or —N($R^7$)— is inserted between methylene groups composing the straight-chain alkylene group can be also produced by the method as described below.

As an example of the epoxy compound wherein $Q^1$ and $Q^2$ are the same or different and each is a straight-chain alkylene group of 1 to 9 carbon atoms, and —O— or —N($R^7$)— is inserted between methylene groups composing the straight-chain alkylene group, an epoxy compound represented by the formula (8):

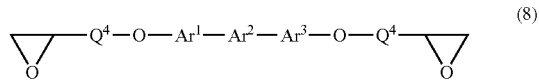

(8)

wherein $Ar^1$, $Ar^2$ and $Ar^3$ are as defined above, $Q^4$ denotes a group represented by the following formula:

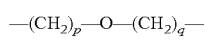

in which p and q each denote an integer of 1 to 8 and the sum of p and q is 9 or less (hereinafter abbreviated as the epoxy compound (8)) is shown and a method for producing said compound is described below. The epoxy compound (8) can be produced, for example, by reacting the compound (3) with the compound represented by the formula (9):

(9)

wherein $X^3$ denotes a halogen atom and p is as defined above, in the presence of a base to obtain a compound represented by the formula (10):

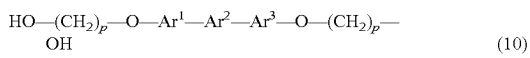

(10)

wherein $Ar^1$, $Ar^2$, $Ar^3$ and p are as defined above, and then reacting the obtained compound represented by the formula (10) with a compound represented by the formula (11):

(11)

wherein $X^4$ denotes a halogen atom and q is as defined above, in the presence of a base.

Examples of the halogen atom include a chlorine atom, a bromine atom, an iodine atom and the like.

Examples of the compound represented by the formula (9) include 2-chloroethanol, 2-bromoethanol, 3-chloropropanol, 4-chlorobutanol, 5-chloropentanol, 6-chlorohexanol, 7-chloroheptanol, 8-chlorooctanol and the like. The amount used of the compound represented by the formula (9) is usually 2 to 100 times, preferably 2 to 10 times the molar amount used of the compound (3).

Examples of the base include inorganic bases, for example, alkali metal hydroxide such as sodium hydroxide and potassium hydroxide, and alkali metal carbonate such as sodium carbonate and potassium carbonate, and the like, and the amount used thereof is usually 2 to 5 times the molar amount used of the compound (3). Such a base may be used as it is or as an aqueous solution.

A reaction of the compound represented by the formula (9) and the compound (3) is usually performed by contacting and mixing the compound represented by the formula (9), the compound (3) and the base in a solvent. The order of mixing them is not particularly limited. The solvent is not particularly limited as long as it is inactive in the reaction, and however, in view of the solubility of the compound (3), aromatic hydrocarbon solvents such as toluene, xylene, ethylbenezene, chlorobenzene and dichlorobenzene, the above-mentioned hydrophilic solvents and mixed solvents thereof are preferred. Among them, ether solvents, aprotic polar solvents and mixed solvents thereof are preferred, and aprotic polar solvents are particularly preferred. The used amount of such a solvent is usually 0.1 to 50 times, preferably 0.5 to 5 times the amount used by weight of the compound (3).

The reaction temperature of the reaction of the compound represented by the formula (9) and the compound (3) is usually 10 to 100° C., preferably 30 to 50° C. The reaction may be performed under normal pressure or reduced pressure.

After completion of the reaction, the compound represented by the formula (10) can be isolated, for example, by adding water and a water-insoluble organic solvent to the reaction liquid if necessary, subjecting the reaction liquid to an extraction treatment, and then concentrating the obtained organic layer.

In a reaction of the compound represented by the formula (10) with the compound represented by the formula (11), the amount used of the compound represented by the formula (11) is usually 2 to 100 times, preferably 2 to 50 times the molar amount used of the compound represented by the formula (10).

Examples of the base are the same as mentioned above, the amount used thereof is usually 2 to 5 times the molar amount used of the compound represented by the formula (10).

The reaction of the compound represented by the formula (10) with the compound represented by the formula (11) is usually performed by contacting and mixing the compound represented by the formula (10), the compound represented by the formula (11) and the base in a solvent. The order of mixing them is not particularly limited. The solvent is not particularly limited as long as it is inactive in the reaction, and however, the above-mentioned hydrophilic solvents are preferred on the ground of that production of by-products tends to be suppressed. Among them, ether solvents, aprotic polar solvents and mixed solvents thereof are preferred, and aprotic polar solvents are particularly preferred. The used amount of such a solvent is usually 0.1 to 50 times, preferably 0.5 to 5 times the amount used by weight of the compound represented by the formula (10).

The reaction temperature of the compound represented by the formula (10) and the compound represented by the formula (11) is usually 10 to 150° C., preferably 30 to 70° C. In the reaction, by-product water is occasionally produced as the reaction progresses. In such case, the reaction is preferably performed while removing by-product water out of the reaction system After completion of the reaction, the epoxy compounds (8) can be isolated, for example, by adding a hydrophilic solvent if necessary, filtering off insolubles and then cooling the filtrate. The isolated epoxy compound (8) may be further purified by a conventional purification means such as recrystallization.

Then, an epoxy composition comprising the epoxy compound (1) and a curing agent is described.

The epoxy composition of the present invention is obtained by mixing the epoxy compound (1) and a curing agent directly or in a solvent. The epoxy composition of the present invention may comprise one type of the epoxy compound (1) and a curing agent, or may comprise different two types or more of the epoxy compounds (1) and a curing agent. Examples of the solvent include ketone solvents such as methyl ethyl ketone and methyl isobutyl ketone; aprotic polar solvents such as dimethyl sulfoxide and N-methylpyrrolidone; ester solvents such as butyl acetate; glycol solvents such as propylene glycol monomethyl ether; and the like.

The curing agent is not particularly limited as long as it has in the molecule at least two functional groups capable of a curing reaction with an epoxy group, and includes an amine curing agent in which the functional groups are amino groups, a phenolic curing agent in which the functional groups are hydroxyl groups, an acid anhydride curing agent in which the functional groups are carboxyl groups, and the like. Among them, the amine curing agent and the phenolic curing agent are preferred.

Examples of the amine curing agent include aliphatic polyvalent amine of 2 to 20 carbon atoms such as ethylenediamine, trimethylenediamine, tetramethylenediamine, hexamethylenediamine, diethylenetriamine and triethylenetetramine; aromatic polyvalent amine such as p-xylenediamine, m-xylenediamine, 1,5-diaminonaphthalene, m-phenylenediamine, p-phenylenediamine, 4,4'-diaminodiphenylmethane, 4,4'-diaminodiphenylethane, 4,4'-diaminodiphenylpropane, 4,4'-diaminodiphenyl ether, 1,1-bis(4-aminophenyl)cyclohexane, 4,4'-diaminodiphenyl sulfone and bis(4-aminophenyl)phenylmethane; alicyclic polyvalent amine such as 4,4'-diaminodicyclohexane and 1,3-bis(aminomethyl)cyclohexane; dicyandiamide and the like. Among them, aromatic polyvalent amine is preferred, and 4,4'-diaminodiphenylmethane, 4,4'-diaminodiphenylethane, 1,5-diaminonaphthalene and p-phenylenediamine are more preferred.

Examples of the phenolic curing agent include phenol resin, phenol aralkyl resin (which has a phenylene skeleton, a diphenylene skeleton or the like), naphthol aralkyl resin, polyoxystyrene resin and the like. Examples of phenol resin include resole phenolic resin such as aniline-modified resole resin and dimethyl ether resole resin; novolac phenolic resin such as phenolic novolac resin, cresol novolac resin, tert-butylphenol novolac resin and nonylphenol novolac resin; special phenolic resin such as dicyclopentadiene-modified phenolic resin, terpene-modified phenolic resin and triphenolmethane resin, and the like. Examples of polyoxystyrene resin include poly(p-oxystyrene) and the like.

Examples of the acid anhydride curing agent include maleic anhydride, phthalic anhydride, pyromellitic anhydride, trimellitic anhydride and the like.

Such a curing agent is used in such an amount that the total number of functional groups capable of a curing reaction with an epoxy group in the curing agent is usually 0.5 to 1.5 times, preferably 0.9 to 1.1 times the total number of epoxy groups in the epoxy compound (1).

The epoxy composition of the present invention may contain, in addition to the epoxy compound (1) and the curing agent, the above-mentioned solvent as described above, or other epoxy compounds or various additives unless the desirable capability of a cured epoxy resin obtained by curing the epoxy composition is impaired. Examples of other epoxy compounds include bisphenol A type epoxy compounds, ortho-cresol type epoxy compounds, biphenol diglycidyl ether, 4,4'-bis(3,4-epoxybutene-1-yloxy)phenyl benzoate, naphthalene diglycidyl ether, α-methylstilbene -4,4'-diglycidyl ether, and the like. Examples of additives include silica powder such as fused crushed silica powder, fused spherical silica powder, crystalline silica powder and secondary agglomerated silica powder; fillers such as alumina, titanium white, aluminum hydroxide, talc, clay, mica and glass fiber; curing accelerators such as triphenylphosphine, 1,8-azabicyclo[5,4,0]-7-undecene and 2-methylimidazole; coupling agents such as γ-glycidoxypropyltrimetoxysilane; coloring agents such as carbon black; low stress components such as silicone oil and silicone rubber; release agents such as natural wax, synthetic wax, higher fatty acid or metallic salts thereof and paraffin; antioxidant and the like. The contents of such other epoxy compounds and additives are not particularly limited as long as they do not impair the desirable capability of a cured epoxy resin obtained by curing the epoxy composition of the present invention.

Next, the cured epoxy resin of the present invention is described. The cured epoxy resin of the present invention can be produced by curing the above-mentioned epoxy composition comprising the epoxy compound (1) and a curing agent. The obtained cured epoxy resin not only exhibits liquid crystallinity, but also has a high thermal conductivity, so that it is useful as an insulating material which requires a high heat dissipation capacity, such as a printed wiring board.

The cured epoxy resin of the present invention may be a cured epoxy resin obtained by curing one type of the epoxy compound (1) and the curing agent, or a cured epoxy resin obtained by curing different two types or more of the epoxy compounds (1) and the curing agent.

A method for producing a cured epoxy resin by curing the above-mentioned epoxy composition includes, for example, a method which comprises heating the epoxy composition as it is up to the predetermined temperature to allow it to cure; a method which comprises heating and melting the epoxy composition, pouring the molten composition into a metal mold or the like, and further heating the mold to mold the composition; a method which comprises melting the epoxy composition, injecting the molten composition into a previously heated metal mold to allow the composition to cure; a method which comprises partially curing the epoxy composition, pulverizing the partially cured product, filling a metal mold with the powder thus obtained and then melt-molding the filled powder; a method which dissolving the epoxy composition in a solvent if necessary, partially curing the composition while stirring, casting the obtained solution, removing the solvent by drying such as ventilation drying or the like, and then heating it for the predetermined time while, if necessary, applying pressure with a pressing machine or the like; and the like.

Finally, prepreg obtained by applying or impregnating the epoxy composition of the present invention to or into a base material, followed by semi-curing is described. Prepreg can be produced by diluting the epoxy composition of the present invention with a solvent if necessary, applying or impregnating the epoxy composition to or into a base material, and then heating the base material to allow the epoxy compounds in the base material to semi-cure. Examples of a base material include woven fabrics or nonwoven fabrics of inorganic fiber such as glass fiber woven fabrics, woven fabrics or nonwoven fabrics of organic fiber such as polyester, and the like. Laminate plates and the like can be easily produced by using such prepreg according to a conventional method.

Hereinafter, the present invention is further illustrated in detail by referring to Examples, but the present invention is not limited to Examples.

EXAMPLE 1

50 parts by weight of 1-(3-methyl-4-hydroxyphenyl)-4-(4-hydroxyphenyl)-1-cyclohexene, 200 parts by weight of epichlorohydrin, 100 parts by weight of dimethyl sulfoxide and 14.8 parts by weight of sodium hydroxide were placed in a 1 L four-necked flask equipped with a thermometer, a condenser tube and a stirring apparatus, decompressed to approximately 6 kPa, and then refluxed and reacted at an internal temperature of approximately 50° C. for 4 hours. The reaction mixture was further heated to an internal temperature of 70° C., and further refluxed and reacted at the temperature for 1 hour. Water produced as the reaction progressed was distilled out of the reaction system.

After the reaction was finished, the reaction mixture was once returned to normal pressure and then decompressed to approximately 7 kPa. Then the reaction mixture was heated to an internal temperature of approximately 70° C. to distill off the remaining epichlorohydrin. After that, 100 parts by weight of dimethyl sulfoxide was added thereto, insolubles were filtered off at an internal temperature of 70° C. The obtained filtrate was cooled to room temperature to precipitate crystals, which were filtered. The filtered crystals were washed with 50 parts by weight of dimethyl sulfoxide and then twice with 100 parts by weight of methanol, and then dried under reduced pressure at 80° C. for 12 hours to obtain 57 parts by weight of 1-(3-methyl-4-oxiranylmethoxyphenyl)-4-(4-oxiranylmethoxyphenyl)-1-cyclohexene. Apparent yield: 81%, purity: 88.7% (LC area percentage value), melting temperature: 117° C.

EXAMPLE 2

30 parts by weight of 1-(3-methyl-4-hydroxyphenyl)-4-(4-hydroxyphenyl)benzene, 120 parts by weight of epichlorohydrin, 60 parts by weight of dimethyl sulfoxide and 9 parts by weight of sodium hydroxide were placed in a 1 L four-necked flask equipped with a thermometer, a cooling pipe and a stirring apparatus, decompressed to approximately 6 kPa, and then refluxed and reacted at an internal temperature of approximately 50° C. for 4 hours. The reaction mixture was further heated to an internal temperature of 70° C., and further refluxed and reacted at the temperature for 1 hour. Water produced as the reaction progressed was distilled out of the reaction system. After the reaction was finished, the reaction mixture was once returned to normal pressure and then decompressed to approximately 7 kPa. Then, the reaction mixture was heated to an internal temperature of approximately 70° C. to distill off the remaining epichlorohydrin. After that, 90 parts by weight of dimethyl sulfoxide was added and insolubles were filtered off at an internal temperature of 70° C. The obtained filtrate was cooled to room temperature to precipitate crystals, which were filtered. The filtered crystals were washed with 45 parts by weight of dimethyl sulfoxide twice and then with 50 parts by weight of methanol, and then dried under reduced pressure at 80° C. for 12 hours to obtain 36 parts by weight of 1-(3-methyl-4-oxiranylmethoxyphenyl)-4-(4-oxiranylmethoxyphenyl) benzene. Apparent yield: 85%, purity: 89.4%, melting temperature: 180° C.

EXAMPLE 3

20 parts by weight of 1-(3-methyl-4-oxiranylmethoxyphenyl)-4-(4-oxiranylmethoxyphenyl)-1-cyclohexene obtained in the above-mentioned Example 1 and 5 parts by weight of 4,4'-diaminodiphenylmethane as a curing agent were mixed to obtain an epoxy composition. The epoxy composition was heated from room temperature up to 180° C. by using a hot stage (manufactured by METTLER-TOLEDO K.K.; FP82HT and FP90) to obtain a cured epoxy resin. When the cured epoxy resin was observed with a polarizing light microscope (manufactured by NIKON CORPORATION; XTP-11), focal conic fan texture was found at approximately 75 to 125° C. Thus it could be confirmed that the cured epoxy resin had liquid crystallinity.

EXAMPLE 4

20 parts by weight of 1-(3-methyl-4-oxiranylmethoxyphenyl)-4-(4-oxiranylmethoxyphenyl)benzene obtained in the above-mentioned Example 2 and 5 parts by weight of 4,4'-diaminodiphenylmethane as a curing agent were mixed to obtain an epoxy composition. The epoxy composition was heated from room temperature up to 250° C. by using a hot stage (manufactured by METTLER-TOLEDO K.K.; FP82HT and FP90) to obtain a cured epoxy resin. When the cured epoxy resin was observed with a polarizing light microscope (manufactured by NIKON CORPORATION; XTP-11), focal conic fan texture was found at approximately 180 to 230° C. Thus it could be confirmed that the cured epoxy resin had liquid crystallinity.

EXAMPLE 5

20 parts by weight of 1-(3-methyl-4-oxiranylmethoxyphenyl)-4-(4-oxiranylmethoxyphenyl)-1-cyclohexene obtained in the above-mentioned Example 1 and 5 parts by weight of 4,4'-diaminodiphenylmethane as a curing agent were mixed to obtain an epoxy composition. The epoxy composition was molten, poured into the plate-like hollow part of a metal mold that had been heated to approximately 110° C., and allowed to stand at approximately 100 to 180° C. for approximately 10 hours to obtain a plate-like cured epoxy resin. A disk having a diameter of 1 cm and a thickness of 1 mm was cut out from the cured epoxy resin, and its thermal conductivities in thickness direction and in-plane direction were measured. A thermal conductivity was calculated from the product of a thermal diffusivity in thickness direction or in-plane direction and a specific heat capacity, which were measured by a laser flash method, and the density of a sample. The thermal conductivity in thickness direction was 0.45 W/m·K and the thermal conductivity in in-plane direction was 0.43 W/m·K.

EXAMPLE 6

20 parts by weight of 1-(3-methyl-4-oxiranylmethoxyphenyl)-4-(4-oxiranylmethoxyphenyl)benzene obtained in the above-mentioned Example 2 and 5 parts by weight of 4,4'-diaminodiphenylmethane as a curing agent were mixed to obtain an epoxy composition. The epoxy composition was molten, poured into the plate-like hollow part of a metal mold that had been heated to approximately 200° C., and allowed to stand at approximately 180 to 220° C. for approximately 10 hours to obtain a plate-like cured epoxy resin. A disk having a diameter of 1 cm and a thickness of 1 mm was cut out from the cured epoxy resin, and its thermal conductivities in thickness direction and in-plane direction were measured by a laser flash method. The thermal conductivity in thickness direction was 0.48 W/m·K and the thermal conductivity in in-plane direction was 0.48 W/m·K.

EXAMPLE 7

20 parts by weight of 1-(3-methyl-4-oxiranylmethoxyphenyl)-4-(4-oxiranylmethoxyphenyl)-1-cyclohexene obtained in the above-mentioned Example 1, 5 parts by weight of 4,4'-diaminodiphenylmethane as a curing agent and 60 parts by weight of alumina (manufactured by Showa Denko K.K., the average particle diameter: 2 μm) as a filler were mixed to obtain an epoxy composition. The epoxy composition was molten, poured into the plate-like hollow part of a metal mold that had been heated to approximately 120° C., and allowed to stand at approximately 100 to 180° C. for approximately 10 hours to obtain a plate-like cured epoxy resin. A disk having a diameter of 1 cm and a thickness of 1 mm was cut out from the cured epoxy resin, and its thermal conductivities in thickness direction and in-plane direction were measured by a laser flash method. The thermal conductivity in thickness direction was 1.6 W/m·K and the thermal conductivity in in-plane direction was 1.5 W/m·K.

EXAMPLE 8

100 parts by weight of 1-(3-methyl-4-oxiranylmethoxyphenyl)-4-(4-oxiranylmethoxyphenyl)-1-cyclohexene obtained in the above-mentioned Example 1, 20 parts by weight of 1,5-diaminonaphthalene (manufactured by Wako Pure Chemical Industries, Ltd.) as a curing agent and 280 parts by weight of methyl ethyl ketone as a solvent were mixed to obtain an epoxy composition (solid content; 30% by weight). The composition was impregnated into a glass fiber woven fabric having a thickness of 0.2 mm and dried by heating to obtain prepreg. Four sheets of the obtained prepreg were laid one on top of another and molded by heating and pressurizing at 100° C. under 4 MPa for 30 minutes and then at 175° C. under 4 MPa for 90 minutes to integrate the sheets, and as a result, a laminate plate having a thickness of 0.8 mm was obtained. A plate-like sample of 60 mm×120 mm was cut out from the laminate plate and its thermal conductivity was measured (the measurement conditions were conformed to a probe method and the measurement was performed at room temperature). The thermal conductivity was 0.80 W/m·K.

COMPARATIVE EXAMPLE 1

28 parts by weight of a bisphenol A type epoxy compound (manufactured by Japan Epoxy Resins Co., Ltd.; EP-828) and 8 parts by weight of 4,4'-diaminodiphenylmethane as a curing agent were mixed to obtain a comparative composition. The comparative composition was heated from room temperature up to 180° C. by using a hot stage (manufactured by METTLER-TOLEDO K.K.; FP82HT and FP90) to obtain a comparative cured epoxy resin. When the comparative cured epoxy resin was observed with a polarizing microscope (manufactured by NIKON CORPORATION; XTP-11), depolarization was not found at a temperature range of room temperature to 180° C. Thus it could be confirmed that the cured epoxy resin did not have liquid crystallinity.

COMPARATIVE EXAMPLE 2

50 parts by weight of the same bisphenol A type epoxy compound as used in Comparative Example 1 and 15 parts by weight of 4,4'-diaminodiphenylmethane as a curing agent were mixed to obtain a comparative composition. The comparative composition was molten, placed in the plate-like hollow part of a metal mold that had been heated to approximately 100° C., and allowed to stand at approximately 100 to 180° C. for approximately 10 hours to obtain a comparative plate-like cured epoxy resin. From the cured epoxy resin, a disk having a diameter of 1 cm and a thickness of 1 mm was cut out, and its thermal conductivities in thickness direction and in-plane direction were measured by a laser flash method. The thermal conductivity in thickness direction was 0.21 W/m·K and the thermal conductivity in in-plane direction was 0.18 W/m·K.

COMPARATIVE EXAMPLE 3

100 parts by weight of the same bisphenol A type epoxy compound as used in Comparative Example 1, 40 parts by weight of 1,5-diaminonaphthalene (manufactured by Wako Pure Chemical Industries, Ltd.) as a curing agent and 327 parts by weight of methyl ethyl ketone as a solvent were mixed to obtain a comparative composition (solid content; 30% by weight). The composition was impregnated into a glass fiber woven fabric having a thickness of 0.2 mm and dried by heating to obtain prepreg. Four sheets of the obtained prepreg were laid one on top of another and molded by heating and pressurizing at 175° C. under 4 MPa for 90 minutes to integrate the sheets, and as a result, a laminate plate having a thickness of 0.8 mm was obtained. A plate-like sample of 60 mm×120 mm was cut out from the laminate plate, and its thermal conductivity was measured (the measurement conditions were conformed to a probe method and the measurement was performed at room temperature). The thermal conductivity was 0.45 W/m·K.

EXAMPLE 9

0.8 part by weight of 1,4-bis(4-hydroxyphenyl)cyclohexane (produced according to a method described in U.S. Pat. No. 3,461,098), 3.2 parts by weight of epichlorohydrin, 3.2 parts by weight of dimethyl sulfoxide and 0.25 part by weight of sodium hydroxide were placed in a 50 ml four-necked flask equipped with a thermometer, a cooling pipe and a stirring apparatus, decompressed to approximately 6 kPa, and then refluxed and reacted at an internal temperature of approximately 50° C. for 4 hours. The reaction mixture was further heated to an internal temperature of 70° C., and then refluxed and reacted at the temperature for 1 hour. Water produced as the reaction progressed was distilled out of the reaction system. After the reaction was finished, the reaction mixture was once returned to normal pressure and then decompressed to approximately 7 kPa. Then, the reaction mixture was heated to an internal temperature of approximately 70° C. to distill off the remaining epichlorohydrin. After that, 3 parts by weight of dimethyl sulfoxide was added to the residue and the mixture was poured into 20 parts by weight of ion-exchange water. Precipitated crystals were filtered, washed with a sufficient amount of ion-exchange water, and then dried under reduced pressure at 80° C. for 12 hours to obtain 0.9 part by weight of 1,4-bis{4-(oxiranylmethoxy)phenyl}cyclohexane. Apparent yield: 83%, purity: 81.5% (LC area percentage value), melting temperature: 154° C.

EXAMPLE 10

20 parts by weight of 1,4-bis{4-(oxiranylmethoxy) phenyl}cyclohexane obtained in Example 9 and 5 parts by weight of 4,4'-diaminodiphenylmethane as a curing agent were mixed to obtain an epoxy composition. The epoxy composition was heated from room temperature up to 180° C. by using a hot stage (manufactured by METTLER-TOLEDO K.K.; FP82HT and FP90) to obtain a cured epoxy resin. When the cured epoxy resin was observed with a polarizing microscope (manufactured by NIKON CORPORATION; XTP-11), sandy texture was found. Thus it could be confirmed that the cured epoxy resin had liquid crystallinity.

EXAMPLE 11

20 parts by weight of 1,4-bis{4-(oxiranylmethoxy) phenyl}cyclohexane obtained in the above-mentioned Example 9 and 5 parts by weight of 4,4'-diaminodiphenylmethane as a curing agent were mixed to obtain an epoxy composition. The epoxy composition was molten, poured into the plate-like hollow part of a metal mold that had been heated to approximately 160° C., and then allowed to stand at approximately 160 to 180° C. for approximately 10 hours to obtain a plate-like cured epoxy resin. A thin-plate sample of 5 mm×10 mm was cut out from the cured epoxy resin and its thermal conductivity was measured (the measurement conditions were conformed to an ac calorimetric method and the measurement was performed at room temperature). The thermal conductivity was 0.40 W/m·K.

INDUSTRIAL APPLICABILITY

As described above, the present invention can provide novel epoxy compounds which have so low melting temperature that they can be melt blended with curing agents at the curing temperature or below, and which are useful as the raw material of cured epoxy resins exhibiting liquid crystallinity. Cured epoxy resins obtained by curing the epoxy compounds with the use of curing agents have high thermal conductivities, so that they can be also used as an insulating material which requires a high heat dissipation capacity, such as a printed wiring board.

The invention claimed is:

1. An epoxy compound represented by the formula (2):

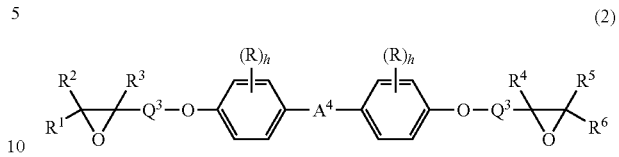

(2)

wherein $A^4$ denotes a divalent group represented by the following formula:

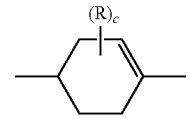

in which R denotes a hydrogen atom or an alkyl group of 1 to 18 carbon atoms, c denotes an integer of 1 to 7, h denotes an integer of 1 to 4, and when more than one R exists in said divalent group, all of R may be the same group or different groups;

$R^1$, $R^2$, $R^3$, $R^4$, $R^5$ and $R^6$ are the same or different and each denotes a hydrogen atom or an alkyl group of 1 to 18 carbon atoms; and $Q^3$ denotes any one of groups represented by the following formulas:

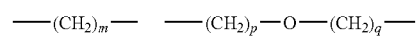

in which m denotes an integer of 1 to 9, p and q denote an integer of 1 to 8, and the sum of p and q is 9 or less, and methylene groups composing the group represented by $Q^3$ are optionally substituted with an alkyl group of 1 to 18 carbon atoms.

2. The epoxy compound according to claim 1, wherein $R^1$, $R^2$, $R^3$, $R^4$, $R^5$ and $R^6$ are hydrogen atoms.

3. An epoxy composition comprising the epoxy compound according to claim 2 and a curing agent.

4. An epoxy composition comprising the epoxy compound according to claim 1 and a curing agent.

5. The epoxy composition according to claim 4, wherein the curing agent is 4,4'-diaminodiphenylmethane, 4,4'-diaminodiphenylethane, 1,5-diaminonaphthalene or p-phenylenediamine.

6. A cured epoxy resin obtained by curing the epoxy composition according to claim 5.

7. A prepreg obtained by applying or impregnating the epoxy composition according to claim 5 to or into a base material, followed by semi-curing.

8. A cured epoxy resin obtained by curing the epoxy composition according to claim 4.

9. A prepreg obtained by applying or impregnating the epoxy composition according to claim 4 to or into a base material, followed by semi-curing.

10. A method for producing an epoxy compound represented by the following formula (2):

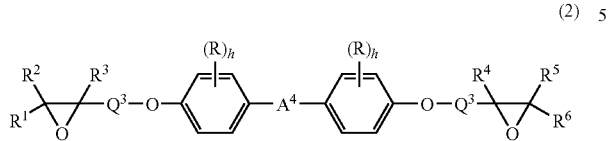
(2)

wherein $A^4$, $R^1$, $R^2$, $R^3$, $R^4$, $R^5$, $R^6$ and $Q^3$ each are as defined below, which comprises reacting a compound represented by the formula:

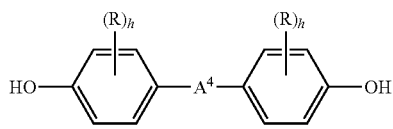

wherein $A^4$ denotes a divalent group represented by the following formula:

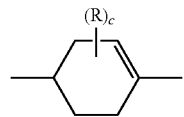

in which R denotes a hydrogen atom or an alkyl group of 1 to 18 carbon atoms, c denotes an integer of 1 to 7, h denotes an integer of 1 to 4, and when more than one R exists in said divalent group, all of R may be the same group or different groups; a compound represented by the formula:

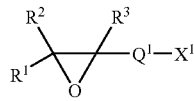

wherein $R^1$, $R^2$ and $R^3$ are the same or different and each denotes a hydrogen atom or an alkyl group of 1 to 18 carbon atoms, $X^1$ denotes a halogen atom, and $Q^3$ denotes any one of groups represented by the following formulas:

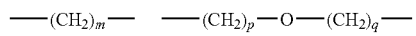

in which m denotes an integer of 1 to 9, p and q denote an integer of 1 to 8, and the sum of p and q is 9 or less, and methylene groups composing the group represented by $Q^3$ are optionally substituted with an alkyl group of 1 to 18 carbon atoms; and a compound represented by the following formula:

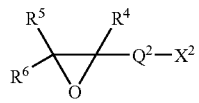

wherein $R^4$, $R^5$ and $R^6$ are the same or different and each denotes a hydrogen atom or an alkyl group of 1 to 18 carbon atoms, $Q^3$ is as defined above, and $X^2$ denotes a halogen atom, in the presence of a base.

* * * * *